US008415115B2

(12) United States Patent
Orenga et al.

(10) Patent No.: US 8,415,115 B2
(45) Date of Patent: Apr. 9, 2013

(54) REACTION MEDIUM FOR METHICILLIN-RESISTANT *STAPHYLOCOCCUS AUREUS* (MRSA) BACTERIA

(75) Inventors: Sylvain Orenga, Neuville sur Ain (FR); Denis Robichon, Blyes (FR); Gilles Zambardi, Trept (FR)

(73) Assignee: Biomerieux, Marcy l'Etoile (FR)

( * ) Notice: Subject to any disclaimer, the term of this patent is extended or adjusted under 35 U.S.C. 154(b) by 0 days.

(21) Appl. No.: 13/062,768

(22) PCT Filed: Oct. 7, 2009

(86) PCT No.: PCT/FR2009/051908
§ 371 (c)(1),
(2), (4) Date: Mar. 8, 2011

(87) PCT Pub. No.: WO2010/040951
PCT Pub. Date: Apr. 15, 2010

(65) Prior Publication Data
US 2011/0165604 A1  Jul. 7, 2011

(30) Foreign Application Priority Data

Oct. 8, 2008  (FR) ..................................... 08 56814

(51) Int. Cl.
*C12Q 1/34* (2006.01)
(52) U.S. Cl. .......................................... 435/18; 435/36
(58) Field of Classification Search ..................... 435/18, 435/36
See application file for complete search history.

(56) References Cited

U.S. PATENT DOCUMENTS

| 6,548,268 | B1 | 4/2003 | Rambach |
| 2003/0235879 | A1 | 12/2003 | Sandberg et al. |
| 2004/0121404 | A1* | 6/2004 | Cotte et al. ..................... 435/7.1 |
| 2004/0235012 | A1 | 11/2004 | Hammann et al. |
| 2007/0292908 | A1* | 12/2007 | Robichon ...................... 435/18 |
| 2008/0145879 | A1 | 6/2008 | Orenga et al. |
| 2009/0017481 | A1 | 1/2009 | Orenga et al. |

FOREIGN PATENT DOCUMENTS

| EP | 0 887 424 A2 | 12/1998 |
| FR | 2 790 765 A1 | 9/2000 |
| FR | 2 881 755 A1 | 8/2006 |
| JP | A-06-217760 | 8/1994 |
| JP | A-07-000181 | 1/1995 |
| WO | WO 02/079486 A2 | 10/2002 |
| WO | WO 2004/027086 A1 | 4/2004 |
| WO | WO 2004/063391 A1 | 7/2004 |
| WO | WO 2007/096639 A2 | 8/2007 |
| WO | WO 2007/099254 A2 | 9/2007 |
| WO | WO 2010/040952 A2 | 4/2010 |

OTHER PUBLICATIONS

Wertheim et al., "Improved Detection of Methicillin-Resistant *Staphylococcus aureus* Using Phenyl Mannitol Broth Containing Aztreonam and Ceftizoxime," *Journal of Clinical Microbiology*, Jul. 2001, pp. 2660-2662, vol. 39, No. 7, American Society for Microbiology.

Velasco et al., "Evaluation of different methods for detecting methicillin (oxacillin) resistance in *Staphylococcus aureus*," *Journal of Antimicrobial Chemotherapy*, Feb. 18, 2005, pp. 379-382, vol. 55, The British Society for Antimicrobial Chemotherapy 2005.

Kluytmans et al., "Performance of CHROMagar Selective Medium and Oxacillin Resistance Screening Agar Base for Identifying *Staphylococcus aureus* and Detecting Methicillin Resistance," *Journal of Clinical Microbiology*, Jul. 2002, pp. 2480-2482, vol. 40, No. 7, American Society for Microbiology.

Merlino et al., "Detection and expression of methicillin/oxacillin resistance in multidrug-resistant and non-multidrug-resistant *Staphylococcus aureus* in Central Sydney, Australia," *Journal of Antimicrobial Chemotherapy*, 2002, pp. 793-801, vol. 49, The British Society for Antimicrobial Chemotherapy.

Gaillot et al., "Evaluation of CHROMagar Staph. Aureus, a New Chromogenic Medium, for Isolation and Presumptive Identification of *Staphylococcus aureus* from Human Clinical Specimens," *Journal of Clinical Microbiology*, Apr. 2000, pp. 1587-1591, vol. 38, No. 4, American Society for Microbiology.

International Search Report for International Patent Application No. PCT/FR2009/051908, mailed on Mar. 9, 2010, (w/ English translation).

Written Opinion for International Patent Application No. PCT/FR2009/051908, mailed on Mar. 9, 2010 (w/ English translation).

Feb. 4, 2011 International Search Report issued in International Patent Application No. PCT/FR2010/051705 (with translation).

Feb. 4, 2011 Written Opinion issued in International Patent Application No. PCT/FR2010/051705 (with translation).

Jun. 1, 2010 International Search Report issued in International Patent Application No. PCT/FR2009/051909 (with translation).

Jun. 1, 2010 Written Opinion of the International Searching Authority issued in International Patent Application No. PCT/FR2009/051909 (with translation).

Manafi et al., "Fluorogenic and Chromogenic Substrates Used in Bacterial Diagnostics," Microbiological Reviews, vol. 55, No. 3, Sep. 1991, pp. 335-348.

Ito, K. et al, "Pharmacokinetics of Cephem Antibiotics in Exudate of Pelvic Retroperitoneal Space After Radical Hysterectomy and Pelvic Lymphadenectomy", Antimicrobial Agents and Chemotherapy, 1990, vol. 34(6), pp. 1160-1164.

Lo, J. et al, "Vancomycin and Amikacin in Cell Cultures for Virus Isolation", Pathology: The Journal of the Royal College of Pathologists of Australasia, 1996, vol. 28(4), pp. 366-369.

Guay, Dr., "Cedrinir: An Advanced-Generation, Broad-spectrum Oral Cephalosporin", Clinical Therapeutics, 2002, vol. 24(4), pp. 473-489.

Perry et al.; "Development and Evaluation of a Chromogenic Agar Medium for Methicillin-Resistant Staphylococcus aureus;" Journal of Clinical Microbiology; Oct. 2004; pp. 4519-4523; vol. 42, No. 10; American Society for Microbiology.

(Continued)

*Primary Examiner* — Susan Hanley
*Assistant Examiner* — Nghi Nguyen
(74) *Attorney, Agent, or Firm* — Oliff & Berridge, PLC

(57) ABSTRACT

A reaction medium for detecting and/or identifying Methicillin-resistant *Staphylococcus aureus* (MRSA) bacteria, comprising a predetermined combination of two antibiotics, a first antibiotic which belongs to the cephalosporin family and a second antibiotic, said first and second antibiotics each being at a sub-inhibitory concentration.

13 Claims, No Drawings

OTHER PUBLICATIONS

Athanasopoulos et al.; "Comparison of three selective chromogenic media for Methicillin-Resistant Staphylococcus aureus detection;" Pathologie Biologie; 2007; pp. 366-369; vol. 55; Elsevier Masson SAS (with Abstract).

Brown et al.; "Guidelines for the laboratory diagnosis and susceptibility testing of methicillin-resistant Staphylococcus aureus(MRSA);" Journal of Antimicrobial Chemotherapy; 2005; pp. 1000-1018; vol. 56; Oxford University Press.

May 24, 2012 Office Action issued in U.S. Appl. No. 13/062,849.
Jun. 21, 2012 Office Action issued in U.S. Appl. No. 12/839,946.
U.S. Appl. No. 13/062,849 in the name of Orenga et al., filed Mar. 8, 2011.
U.S. Appl. No. 12/839,946 in the name of Roche et al., filed Jul. 20, 2010.
Dec. 3, 2012 Office Action issued in U.S. Appl. No. 13/062,849.
Jan. 7, 2013 Office Action issued in U.S. Appl. No. 12/839,946.

* cited by examiner

REACTION MEDIUM FOR METHICILLIN-RESISTANT *STAPHYLOCOCCUS AUREUS* (MRSA) BACTERIA

The present invention relates to a culture medium for detecting Methicillin-resistant *Staphylococcus aureus* (MRSA) bacteria. The invention also relates to the use of this medium, and to a method for identifying MRSA bacteria. Methicillin-resistant *Staphylococcus aureus* are *Staphylococcus aureus* strains characterized by their resistance to an antibiotic, Methicillin, and to related antibiotics such as Oxacillin. This resistance is most commonly conferred by the expression of a gene mecA, leading to the production of a modified protein, PLP2a (also known as PBP 2a or PBP 2'). MRSA bacteria represent a high percentage of nosocomial infections, and are often responsible for serious and potentially deadly health problems. MRSAs, which are most commonly cross-transmitted between patients via care staff, are very contagious and responsible for endemic infections that are very difficult to control.

In addition to a suitable treatment, screening for MRSA carriers and the isolation of colonized patients constitute the most effective method that is today recommended by official organizations such as the Society for Healthcare Epidemiology of America. Early and systematic screening is therefore essential.

MRSAs can be detected by various techniques.

It is thus possible to detect MRSAs by molecular biology techniques. In this respect, mention may be made in particular of application EP887424. However, such methods remain expensive in the routine test and require qualified staff.

It is also possible to use conventional culture media for detecting *Staphylococcus aureus*, such as the medium described in application EP 1390524. The detection of MRSA is carried out in an additional step, by means of a specific agglutination test (Slidex MRSA, bioMérieux) or by means of an agar diffusion method in the presence of an Oxacillin disc (recommendations of the Comité de l'Antibiogramme de la Société Française de Microbiologie [Antibiogram Committee of the French Society for Microbiology]).

It is also possible to culture bacteria that may be MRSAs on agar media in the presence of antibiotics. Such media may also be chromogenic, which facilitates the reading and the detection of MRSAs. Mention may in particular be made of the medium described in application EP 1543147. However, since the detection of a phosphatase activity under the conditions described is not very specific, it is necessary to combine it with the detection of several other enzymatic activities, thereby reducing the fertility of the medium and increasing the cost thereof.

The invention proposes to solve the gaps in the prior art by providing a new sensitive, specific and rapid detection medium for isolating and identifying Methicillin-resistant *Staphylococcus aureus* (MRSA).

Surprisingly, the inventors have demonstrated that the use of a combination of antibiotics, at a low and predetermined concentration, makes it possible to obtain an excellent detection medium for isolating and identifying Methicillin-resistant *Staphylococcus aureus* (MRSA). This effect is all the more surprising since the antibiotics, used separately, do not in any way make it possible to differentiate MRSAs at the concentrations according to the invention.

Before proceeding further, the following definitions, which are in no way limiting, will make it possible to understand the invention more clearly.

For the purpose of the present invention, the term reaction medium is intended to mean a medium comprising all the elements necessary for the survival and/or growth of microorganisms, such as *Staphylococcus aureus*.

This reaction medium may either serve as a revealing medium only, or as a culture and revealing medium. In the first case, the microorganisms are cultured before inocculation, and in the second case, the reaction medium also constitutes the culture medium.

The reaction medium may be solid, semi-solid or liquid. The term "solid medium" is intended to mean, for example, a gelled medium. Preferably, the medium according to the invention is a gelled medium. Agar is the conventional gelling agent in microbiology for culturing microorganisms, but it is possible to use gelatine or agarose. A certain number of preparations are commercially available, for instance Colombia agar, Trypticase-soy agar, MacConkey agar, Sabouraud agar, or more generally those described in the Handbook of Microbiological Media (CRC Press).

The reaction medium according to the invention may contain other possible additives, for instance: peptones, one or more growth factors, carbohydrates, one or more selective agents, buffer solutions, one or more gelling agents, etc. This reaction medium may be in the form of a liquid or of a gel that is ready to use, i.e. ready for inocculation in a tube or flask or on a Petri dish. When this medium is provided in the form of a gel in a flask, the medium is preferably regenerated (subjected to 100° C.) before being poured into a Petri dish.

Preferably, the medium according to the invention is a selective medium, i.e. a medium comprising inhibitors which favour the growth of *Staphylococcus aureus* bacteria. Mention may in particular be made of lithium chloride (LiCl), sodium azide ($NaN_3$), colistin, amphotericin, aztreonam, colimycin, sodium chloride (NaCl), deferoxamine, and the vibriostatic compound O/129.

For the purpose of the present invention, the substrate for an enzymatic or metabolic activity is selected from any substrate that can be hydrolysed to give a product which enables the direct or indirect detection of an enzymatic activity or of a metabolism, such as, in particular, an osidase activity, preferably an alpha-glucosidase or esterase activity, preferably a phosphatase or peptidase activity, preferably a coagulase activity, or the metabolism of a carbohydrate, preferably mannitol.

It may be a natural or synthetic substrate. The metabolism of the substrate causes a variation in the physicochemical properties of the reaction medium or of the cells of organisms. This variation can be detected by physicochemical methods, in particular optical methods, visually by the operator or using spectrometric, electrical, magnetic, etc., instruments. Preferably, it is a variation in the optical properties, such as a modification of absorption, of fluorescence or of luminescence.

As a chromogenic substrate, mention may in particular be made of substrates based on indoxyl, flavone, alizarine, acridine, phenoxazine, nitrophenol, nitroaniline, naphthol, catechol, hydroxyquinoline or coumarin. Preferably, the substrate(s) used in the present invention is (are) indoxyl-based. As a fluorescent substrate, mention may in particular be made of substrates based on umbelliferone or on coumarin, based on resorufin, phenoxazine, naphthol, naphthylamine, 2'-hydroxyphenyl-heterocycle or 2'-aminophenyl-heterocycle, or else based on fluorescein. As a substrate for alpha-glucosidase enzymatic activity, mention may more particularly be made of the substrates 5-bromo-6-chloro-3-indoxyl-alpha-glucoside; dihydroxyflavone-alpha-glucoside; 3,4-cyclohexenoesculetine-alpha-glucoside; 8-hydroxiquinoline-alpha-glucoside; 5-bromo-4-chloro-3-indoxyl-alpha-glucoside; 5-bromo-4-chloro-3-indoxyl-N-methyl-alpha-glucoside; 6-chloro-3-indoxyl-alpha-glucoside; 5-bromo-3-indoxyl-alpha-glucoside; 5-iodo-3-indoxyl-alpha-glucoside; 6-fluoro-3-indoxyl-alpha-glucoside; alizarine-alpha-glucoside; nitrophenyl-alpha-glucoside; 4-methylumbelliferyl-alpha-glucoside; naphtholbenzein-alpha-glucoside; indoxyl-N- methyl-alpha-glucoside; naphtyl-alpha-glucoside; aminophenyl-alpha-glucoside; dichloroaminophenyl-alpha-glucoside.

Preferably, the substrate used in the present invention is 5-bromo-4-chloro-3-indoxyl-alpha-glucoside, preferably in combination with 5-bromo-4-chloro-3-indoxyl-N-methyl-alpha-glucoside.

As a substrate for phosphatase enzymatic activity, mention may more particularly be made of the substrates 5-bromo-6-chloro-3-indoxyl phosphate; 3,4-cyclohexenoesculetin phosphate; 5-bromo-4-chloro-3-indoxyl phosphate; 5-bromo-4-chloro-3-indoxyl-N-methyl phosphate; 6-chloro-3-indoxyl phosphate; 5-bromo-3-indoxyl phosphate; 5-iodo-3-indoxyl phosphate; 6-fluoro-3-indoxyl phosphate; nitrophenyl phosphate; 4-methylumbelliferyl phosphate; indoxyl-N-methyl phosphate; naphthyl phosphate.

As a coagulase substrate, mention may more particularly be made of the substrates Boc-Val-Pro-Arg-7-amido-4-methylcoumarin, Bz-Phe-Val-Arg-p-nitroanilide, Z-Gly-Pro-Arg-4-methoxy-beta-naphthylamide and plasminogen. In general, these substrates are used in combination with a source of prothrombin, such as purified prothrombin or blood plasma. The substrate used in the present invention may be in combination with other substrates, such as a substrate for an osidase, and in particular beta-glucosidase or beta-ribosidase, an esterase, and in particular a phosphatase or a phospholipase, a peptidase, and in particular a coagulase. The substrates of the invention can be used in a wide pH range, in particular between pH 5.5 and 10, preferably between 6.5 and 10. When the medium according to the invention comprises a substrate or several substrates for alpha-glucosidase enzymatic activity, the concentration of substrate(s) is preferably between 0.01 and 2 g/l, even more preferably between 0.02 and 0.2 g/l, and is advantageously 0.1 g/l. This is because, at this substrate concentration, a better coloration contrast is obtained.

The substrate may also be a metabolic substrate, such as a carbon source, coupled to an indicator that produces a coloration in the presence of one of the metabolism products. In the case of the metabolism of a carbohydrate, it is preferably mannitol coupled to a pH indicator.

For the purpose of the present invention, an antibiotic which belongs to the cephalosporin family is an antibiotic preferably selected from:
- a first-generation cephalosporin, such as: Cefalexin, Cefaloridine, Cefalotin, Cefazolin, Cefadroxil, Cefazedone, Cefatrizin, Cefapirin, Cefradine, Cefacetrile, Cefrodaxine, Ceftezole;
- a second-generation cephalosporin, such as: Cefoxitin, Cefuroxime, Cefamandole, Cefaclor, Cefotetan, Cefonicide, Cefotiam, Loracarbef, Cefmetazole, Cefprozil, Ceforanide;
- a third-generation cephalosporin, such as: Cefotaxime, Ceftazidime, Cefsulodine, Ceftriaxone, Cefmenoxime, Latamoxef, Ceftizoxime, Cefixime, Cefodizime, Cefetamet, Cefpiramide, Cefoperazone, Cefpodoxime, Ceftibuten, Cefdinir, Cefditoren, Ceftriaxone, Cefoperazone, Cefbuperazone;
- a fourth-generation cephalosporin, such as Cefepime, Cefpirome.

Cephamycins such as Cefoxitin, Cefotetan, Cefmetazole, Cefbuperazone or Latamoxef are a cephalosporin subfamily. In the context of the present invention, the antibiotic which belongs to the cephalosporin family is preferably Cefoxitin, and may be in combination with Cefotaxime.

For the purpose of the present invention, an antibiotic which belongs to the carbapenem family is an antibiotic preferably selected from Meropenem, Ertapenem, Imipenem, Doripenem, Faropenem.

In the context of the present invention, the antibiotic which belongs to the carbapenem family is preferably Ertapenem.

For the purpose of the present invention, an antibiotic which belongs to the aminoglycoside family is an antibiotic preferably selected from Amikacin, Gentamicin, Isepamicin, Kanamycin, Netilmicin, Streptomycin, Tobramycin.

The sub-inhibitory concentration is intended to mean a concentration below the concentration of antibiotic required for inhibition of MSSAs, in a culture medium suitable for searching for *S. aureus* using a biological sample, such as the chromID™ *S. aureus* medium (bioMerieux). This concentration is below approximately 3 mg/l in the case of Cefoxitin, approximately 2 mg/l in the case of Cefotaxime, approximately 1 mg/l in the case of Ertapenem, approximately 2 mg/l in the case of Cefoperazone, approximately 2 mg/l in the case of Cefpodoxime, and approximately 1 mg/l in the case of Cefdinir.

The term predetermined combination of two antibiotics is intended to mean a combination of two particular antibiotics, each of the two being at a particular sub-inhibitory concentration. Such a combination can be determined in particular by the test of example A.

The term biological sample is intended to mean a clinical sample, derived from a bronchial, tracheal or pulmonary aspiration sample or a pleural fluid sample, from broncho-alveolar lavage, from expectorations, from blood or from a lung biopsy, from joint fluid or pericardial fluid; biological fluid or a food sample, derived from any type of food. This sample may thus be liquid or solid and mention may be made, in a nonlimiting manner, of a clinical sample from blood, plasma, urine or faeces, or from samples taken from the nose, from the perineum, from the throat, from the skin, from wounds or from cerebrospinal fluid, or a food sample.

In this respect, the invention relates to a reaction medium for detecting and/or identifying Methicillin-resistant *Staphylococcus aureus* (MRSA) bacteria, comprising a predetermined combination of two antibiotics, a first antibiotic which belongs to the cephalosporin family and a second antibiotic, said first and second antibiotics each being at a sub-inhibitory concentration.

According to one preferred embodiment of the invention, said first antibiotic belongs to the cephamycin subfamily. According to one more preferred embodiment of the invention, said first antibiotic is Cefoxitin.

According to one preferred embodiment of the invention, said second antibiotic belongs to the carbapenem family. According to one preferred embodiment of the invention, said second antibiotic belongs to the cephalosporin family. According to one preferred embodiment of the invention, said second antibiotic belongs to the aminoglycoside family.

According to one preferred embodiment of the invention, the medium also comprises a substrate for detecting an enzymatic activity, preferably an osidase, esterase or peptidase activity, or a metabolic activity, preferably the metabolism of a carbohydrate.

In the case of an osidase activity, it is preferably an alpha-glucosidase activity. In the case of an esterase activity, it is preferably a phosphatase activity. In the case of a peptidase activity, it is preferably a coagulase activity. In the case of the metabolism of a carbohydrate, it is preferably mannitol coupled to a pH indicator.

According to one preferred embodiment of the invention, the substrate is a substrate for detecting an osidase, preferably alpha-glucosidase, enzymatic activity.

Said substrate for an alpha-glucosidase enzymatic activity is preferably an indoxyl-alpha-glucoside. Preferably, the substrate used is 5-bromo-4-chloro-3-indoxyl-N-methyl-alpha-glucoside (X-N-methyl-alpha-glucoside). Preferably, this substrate is present in the medium at a concentration of between 0.01 and 2 g/l preferably between 0.02 and 0.3 g/l.

According to one particular embodiment of the invention, said medium comprises a second enzymatic or metabolic substrate. This substrate may be an alpha-glucosidase substrate or another substrate. Preferably, this second substrate is an alpha-glucosidase substrate.

When said medium comprises a second alpha-glucosidase substrate, this substrate is preferably 5-bromo-4-chloro-3-indoxyl-alpha-glucoside (X-alpha-glucoside). Preferably, this second substrate is present in the medium at a concentration of between 0.01 and 2 g/l preferably between 0.02 and 0.3 g/l.

According to one preferred embodiment of the invention, said first and/or second antibiotic(s) belonging to the cephalosporin family is selected from:
- a first-generation cephalosporin, preferably Cefalexin, Cefaloridine, Cefalotin, Cefazolin, Cefadroxil, Cefazedone, Cefatrizine, Cefapirin, Cefradine, Cefacetrile, Cefrodaxine, Ceftezole;
- a second-generation cephalosporin, preferably Cefoxitin, Cefuroxime, Cefamandole, Cefaclor, Cefotetan, Cefonicide, Cefotiam, Loracarbef, Cefmetazole, Cefprozil, Ceforanide;
- a third-generation cephalosporin, preferably Cefotaxime, Ceftazidime, Cefsulodine, Ceftriaxone, Cefmenoxime, Latamoxef, Ceftizoxime, Cefixime, Cefodizime, Cefetamet, Cefpiramide, Cefoperazone, Cefpodoxime, Ceftibuten, Cefdinir, Cefditoren, Ceftriaxone, Cefoperazone, Cefbuperazone;
- a fourth-generation cephalosporin, preferably Cefepime, Cefpirome.

According to one preferred embodiment of the invention, said second antibiotic belonging to the carbapenem family is selected from Meropenem, Ertapenem and Imipenem.

According to one preferred embodiment of the invention, the combination of two antibiotics is selected from the combinations Cefoxitin-Cefotaxime or Cefoxitin-Ertapenem.

According to one preferred embodiment of the invention, the medium may also comprise at least one inhibitor which favours the growth of Staphylococcus aureus bacteria, such as lithium chloride (LiCl), sodium azide ($NaN_3$), Colistin, Amphotericin, Aztreonam, Colimycin, sodium chloride (NaCl) and Deferoxamine.

According to one preferred embodiment of the invention, the medium also comprises a mixture of inhibitors, comprising four inhibitors, which favours the growth of bacteria of the Staphylococcus genus, said inhibitors being LiCl, vibriostatic compound O/129, Aztreonam and Amphotericin.

According to one preferred embodiment of the invention, the combination of two antibiotics comprises Cefoxitin and Cefotaxime. Preferably, said sub-inhibitory concentration of Cefoxitin is between 0.25 and 1.5 mg/l, preferably between 0.5 and 1 mg/l. Preferably, said sub-inhibitory concentration of Cefotaxime is between 0.25 and 1.5 mg/l, preferably between 0.5 and 1 mg/l.

According to one preferred embodiment of the invention, the combination of two antibiotics comprises Cefoxitin and Ceftriaxone. Preferably, said sub-inhibitory concentration of Cefoxitin is between 0.25 and 1.5 mg/l preferably between 0.5 and 1 mg/l. Preferably, said sub-inhibitory concentration of Ceftriaxone is between 0.25 and 1.5 mg/l preferably between 0.5 and 1 mg/l.

According to one preferred embodiment of the invention, the combination of two antibiotics comprises Cefoxitin and Ertapenem. Preferably, said sub-inhibitory concentration of Cefoxitin is between 0.25 and 1.5 mg/l preferably between 0.5 and 1 mg/l. Preferably, said sub-inhibitory concentration of Ertapenem is between 0.5 and 0.75 mg/l.

According to one preferred embodiment of the invention, the combination of two antibiotics comprises Cefoxitin and Cefpodoxime. Preferably, said sub-inhibitory concentration of Cefoxitin is between 0.25 and 1.5 mg/l, preferably between 0.5 and 1 mg/l. Preferably, said sub-inhibitory concentration of Cefpodoxime is between 0.75 and 1 mg/l preferably between 0.5 and 1 mg/l.

According to one preferred embodiment of the invention, the combination of two antibiotics comprises Cefoxitin and Cefoperazone. Preferably, said sub-inhibitory concentration of Cefoxitin is between 0.25 and 1.5 mg/l preferably between 0.5 and 1 mg/l. Preferably, said sub-inhibitory concentration of Cefoperazone is between 0.5 and 0.75 mg/l preferably between 0.75 and 1 mg/l.

According to one preferred embodiment of the invention, the combination of two antibiotics comprises Cefoxitin and Cefdinir. Preferably, said sub-inhibitory concentration of Cefoxitin is between 0.25 and 1.5 mg/l preferably between 0.25 and 0.75 mg/l. Preferably, said sub-inhibitory concentration of Cefdinir is between 0.05 and 0.5 mg/l, preferably between 0.1 and 0.25 mg/l.

The invention also relates to the in vitro use of a reaction medium as defined above, for isolating and identifying Methicillin-resistant Staphylococcus aureus (MRSA) bacteria. When this medium is used, the MRSAs are preferably detected by means of a specific α-glucosidase activity which makes it possible to obtain coloured or fluorescent colonies. The other Staphylococcus aureus species appear colourless or have a different colour or fluorescence from that of the S. aureus colonies.

Finally, the invention relates to a method for detecting and/or identifying Methicillin-resistant Staphylococcus aureus (MRSA) bacteria, in a biological sample, comprising:
a) inocculating the biological sample that may contain Methicillin-resistant Staphylococcus aureus (MRSA) bacteria on a reaction medium as defined above;
b) incubating;
c) identifying the MRSA colonies.

The incubation is preferably carried out at a temperature of between 30° C. and 42° C. The MRSAs are preferably detected by means of a specific α-glucosidase activity which makes it possible to obtain coloured or fluorescent colonies. The other Staphylococcus species appear colourless or have a different colour or fluorescence from that of the S. aureus colonies.

The following examples are given by way of illustration and are in no way limiting in nature. They will make it possible to understand the invention more clearly.

EXAMPLE A

Test For Determining the Predetermined Combination of Two Antibiotics According To the Invention The test below can be carried out in order to define the predetermined combination of two antibiotics according to the invention, which depends on the antibiotics used and, more generally, on the formulation of said reaction medium. To aid the understanding of this test, it is carried out below in the case of a combination of Cefoxitin and Cefotaxime, using a kit of microorganism strains, comprising MSSAs and MRSAs, but this test can of course be carried out for other antibiotics.

Ten reaction media suitable for searching for S. aureus in a biological sample (such as a chromID™ S. aureus medium, bioMérieux) and various concentrations of Cefoxitin (between 0 and 3 mg/l) and Cefoxatime (between 0 and 2 mg/l) are used to obtain antibiotic concentrations of between 0 and 5 mg/l. The various concentrations are evenly spaced out, for example according to an arithmetic or geometric distribution. Each of the media is aliquoted in such a way that each microorganism strain can be inoculated in culture pure, on each of the media. After a suitable incubation time, preferably 18 to 24 hours, at an appropriate temperature, preferably 30 to 37° C., the media are examined so as to select the medium comprising a combination of Cefoxitin and Cefotaxime which makes it possible to reveal the greatest number of MRSAs while at the same time differentiating them from the greatest number of MSSA strains.

It may be necessary to repeat the experiment with the concentrations of each of the antibiotics being adjusted.

EXAMPLE B

Medium According To the Invention Comprising An Alpha-Glucosidase Substrate

1. Preparation of the medium according to the invention

The media tested in the experiments hereinafter were media comprising the chromID MRSA medium (bioMérieux ref. 43 451) as basic medium, and comprising the following elements:

Medium T: chromID MRSA control medium (ref. 43 451), comprising in particular an X-N-methyl-alpha-glucoside substrate, at a concentration of 0.1 g/l, and Cefoxitin at 4 mg/l.

Medium S: medium T, also comprising an X-alpha-glucoside substrate, at a concentration of 25, 37, 45 or 50 mg/l.

Medium A: medium S (X-alpha-glucoside concentration: 45 mg/l), the Cefoxitin being substituted with Ceftriaxone, at a concentration of 1, 2, 4, 8, 16, 32 mg/l.

Medium B: medium S (X-alpha-glucoside concentration: 45 mg/l), the Cefoxitin being substituted with Cefotaxime at a concentration of 1, 2, 4, 8, 16, 32 mg/l.

Medium C: medium S (X-alpha-glucoside concentration: 45 mg/l), the Cefoxitin being substituted with Ertapenem at a concentration of 0.1, 0.25, 0.5, 0.75, 1 mg/l.

Medium D: medium S (X-alpha-glucoside concentration: 45 mg/l), the Cefoxitin being substituted with Cefoperazone at a concentration of 0.5, 1, 1.5, 2 mg/l.

Medium E: medium S (X-alpha-glucoside concentration: 45 mg/l), the Cefoxitin being substituted with Cefpodoxime at a concentration of 0.5, 1, 1.5, 2 mg/l.

Medium F: medium S (X-alpha-glucoside concentration: 45 mg/l), the Cefoxitin being substituted with a Cefoxitin/Cefotaxime concentration at the concentrations below:

| [Cefoxitin] in mg/l | 0.5 | 0.5 | 1 | 1 |
|---|---|---|---|---|
| [Cefotaxime] in mg/l | 0.5 | 1 | 0.5 | 1 |

Medium G: medium S (X-alpha-glucoside concentration: 45 mg/l), the Cefoxitin being substituted with a Cefoxitin/Ceftriaxone combination at the concentrations below:

| [Cefoxitin] in mg/l | 0.5 | 0.5 | 1 | 1 |
|---|---|---|---|---|
| [Ceftriaxone] in mg/l | 0.5 | 1 | 0.5 | 1 |

Medium H: medium S (X-alpha-glucoside concentration: 45 mg/l), the Cefoxitin being substituted with a Cefoxitin/Ertapenem combination at the concentrations below:

| [Cefoxitin] in mg/l | 0.5 | 0.5 | 0.5 | 0.5 | 0.75 | 0.75 | 0.75 | 0.75 |
|---|---|---|---|---|---|---|---|---|
| [Ertapenem] in mg/l | 0.25 | 0.5 | 0.75 | 1 | 0.25 | 0.5 | 0.75 | 1 |

Medium I: medium S (X-alpha-glucoside concentration: 45 mg/l), the Cefoxitin being substituted with a Cefoxitin/Cefpodoxime combination at the concentrations below:

| [Cefoxitin] in mg/l | 0.5 | 0.5 | 0.5 | 0.5 | 0.75 | 0.75 | 0.75 | 0.75 |
|---|---|---|---|---|---|---|---|---|
| [Cefpodoxime] in mg/l | 0.5 | 1 | 1.5 | 2 | 0.5 | 1 | 1.5 | 2 |

Medium J: medium S (X-alpha-glucoside concentration: 45 mg/l), the Cefoxitin being substituted with a Cefoxitin/Cefoperazone combination at the concentrations below:

| [Cefoxitin] in mg/l | 0.5 | 0.5 | 0.5 | 0.5 | 0.75 | 0.75 | 0.75 | 0.75 |
|---|---|---|---|---|---|---|---|---|
| [Cefoperazone] in mg/l | 0.5 | 0.75 | 1 | 1.5 | 0.5 | 0.75 | 1 | 1.5 |

Medium K: medium S (X-alpha-glucoside concentration: 45 mg/l), the Cefoxitin being substituted with a Cefoxitin/Cefotaxime combination, at the concentrations below, also comprising a mixture of inhibitors that favour the growth of Staphylococcus aureus.

| [Cefoxitin] in mg/l | 0.75 | 0.75 | 0.75 | 0.75 | 0.75 | 0.75 |
|---|---|---|---|---|---|---|
| [Cefotaxime] in mg/l | 0.5 | 0.55 | 0.6 | 0.65 | 0.7 | 0.75 |

Medium L: medium S (X-alpha-glucoside concentration: 45 mg/l), the Cefoxitin being substituted with Cefdinir at a concentration of 0.25, 0.5, 1, 2, 4, 8 mg/l.

Medium M: medium S (X-alpha-glucoside concentration: 45 mg/l), the Cefoxitin being substituted with a Cefoxitin/Cefdinir combination at the concentrations below:

| [Cefoxitin] in mg/l | 0.25 | 0.5 | 0.75 | 0.25 | 0.5 | 0.75 | 0.25 | 0.5 | 0.75 |
|---|---|---|---|---|---|---|---|---|---|
| [Cefdinir] in mg/l | 0.1 | 0.1 | 0.1 | 0.25 | 0.25 | 0.25 | 0.5 | 0.5 | 0.5 |

2. Inocculation And Reading of Media

Various sets of bacterial strains, all derived from the Applicant's collection, suspended in physiological saline, were inocculated so as to give isolated colonies on the medium. The dishes were incubated at 37° C. for 48 hours. The colonies formed were examined visually after 18 h or 24 hours of incubation. The coloration intensity was also observed according to a scale of 0 to 4 (0: no coloration, 4: very intense coloration).

The strains detected correspond to the strains forming colored colonies on the medium.

3. Results 3.1 Medium For Detecting MRSAs, Comprising Two Alpha-Glucosidase Substrates The results obtained during the use of one or two alpha-glucosidase substrates are given in table 1.

TABLE 1

Intensity of colouration of the colonies during the use of two alpha-glucosidase substrates

| Strains | Incubation | Medium T Intensity of green coloration | Medium S [X α Glu] = 25 mg/l Intensity of green coloration | Medium [X α Glu] = 37 mg/l Intensity of green coloration | Medium [X α Glu] = 50 mg/l Intensity of green coloration |
|---|---|---|---|---|---|
| MRSA | 18 h | 2 | 2 | 2.5 | 3 |
|  | 24 h | 2 | 2 | 3 | 3 |
|  | >40 h | 2 | 2.5 | 3 | 3 |
| MRSA | 18 h | 0 | 0 | 0 | 0 |
|  | 24 h | 2 | 2 | 2.5 | 3 |
|  | >40 h | 3 | 3 | 4 | 4 |
| MRSA | 18 h | 1.5 | 1.5 | 2 | 3 |
|  | 24 h | 2 | 2 | 4 | 4 |
|  | >40 h | 2 | 3 | 4 | 4 |
| MRSA | 18 h | 2 | 2 | 3 | 3 |
|  | 24 h | 2 | 2 | 4 | 4 |
|  | >40 h | 2.5 | 2.5 | 4 | 4 |
| MRSA | 18 h | 0.5 | 0.5 | 0 | 0 |
|  | 24 h | 1 | 0.5 | 1.5 | 2.5 |
|  | >40 h | 2.5 | 3 | 4 | 4 |
| MRSA | 18 h | 2 | 2 | 2.5 | 3 |
|  | 24 h | 2.5 | 2.5 | 2.5 | 2.5 |
|  | >40 h | 2.5 | 3 | 4 | 4 |
| MRSA | 18 h | 0 | 0 | 0 | 0 |
|  | 24 h | 1 | 1 | 3 | 4 |
|  | >40 h | 2 | 3 | 4 | 4 |
| MRSA | 18 h | 0 | 0 | 0 | 0 |
|  | 24 h | 0 | 0 | 0 | 0 |
|  | >40 h | 3 | 3 | 4 | 4 |
| MRSA | 18 h | 1.5 | 1.5 | 3 | 2.5 |
|  | 24 h | 2 | 2 | 4 | 4 |
|  | >40 h | 2.5 | 3 | 4 | 4 |
| MRSA | 18 h | 0 | 0 | 0 | 0 |
|  | 24 h | 0 | 0 | 2 | 3 |
|  | >40 h | 2.5 | 3 | 4 | 4 |

The addition of a second alpha-glucosidase substrate made it possible to strongly intensify the coloration of the colonies, thus making it possible to achieve better pinpointing of the MRSA colonies.

3.2 Medium For Detecting MRSAs, Comprising An Antibiotic Selected From Ceftriaxone, Cefotaxime, Ertapenem, Cefoperazone, Cefpodoxime or Cefdinir The results obtained when the Cefoxitin was substituted with another antibiotic are given in tables 2a to 2f.

TABLE 2a

Substitution of Cefoxitin with Ceftriaxone

| | Medium | T | A | | | | |
|---|---|---|---|---|---|---|---|
| | Antibiotic | Cefoxitin | Ceftriaxone | | | | |
| | Concentration (mg/l) | 4 | 1 | 2 | 4 | 8 | 16 32 |
| MRSA (No. of strains | Reading 18 h | 7/10 | 9/10 | 8/10 | 3/10 | | |
| detected/No. of strains) | Reading 24 h | 8/10 | 10/10 | 10/10 | 6/10 | 3/10 | |
| MSSA (No. of strains | Reading 18 h | 3/10 | 9/10 | 7/10 | 3/10 | | |
| detected/No. of strains) | Reading 24 h | 3/10 | 9/10 | 7/10 | 3/10 | | |

TABLE 2b

Substitution of Cefoxitin with Cefotaxime

| | Medium | T | B | | | | |
|---|---|---|---|---|---|---|---|
| | Antibiotic | Cefoxitin | Cefotaxime | | | | |
| | Concentration (mg/l) | 4 | 1 | 2 | 4 | 8 | 16 32 |
| MRSA (No. of strains | Reading 18 h | 7/10 | 6/10 | 3/10 | 1/10 | | |
| detected/No. of strains) | Reading 24 h | 9/10 | 9/10 | 5/10 | 3/10 | | |
| MSSA (No. of strains | Reading 18 h | 3/10 | 7/10 | 3/10 | | | |
| detected/No. of strains) | Reading 24 h | 3/10 | 7/10 | 3/10 | | | |

TABLE 2c

Substitution of Cefoxitin with Ertapenem

| | Medium | T | C | | | | |
|---|---|---|---|---|---|---|---|
| | Antibiotic | Cefoxitin | Ertapenem | | | | |
| | Concentration (mg/l) | 4 | 0.1 | 0.25 | 0.5 | 0.75 | 1 |
| MRSA (No. of strains | Reading 18 h | 7/10 | 9/10 | 9/10 | 8/10 | 8/10 | 5/10 |
| detected/No. of strains) | Reading 24 h | 7/10 | 10/10 | 10/10 | 10/10 | 9/10 | 9/10 |
| MSSA (No. of strains | Reading 18 h | | 10/10 | 10/10 | 10/10 | 8/10 | 4/10 |
| detected/No. of strains) | Reading 24 h | | 10/10 | 10/10 | 10/10 | 9/10 | 6/10 |

TABLE 2d

Substitution of Cefoxitin with Cefoperazone

| | Medium | T | D | | | |
|---|---|---|---|---|---|---|
| | Antibiotic | Cefoxitin | Cefoperazone | | | |
| | Concentration (mg/l) | 4 | 0.5 | 1 | 1.5 | 2 |
| MRSA (No. of strains | Reading 18 h | 5/10 | 8/10 | 8/10 | 5/10 | 4/10 |
| detected/No. of strains) | Reading 24 h | 5/10 | 10/10 | 8/10 | 6/10 | 5/10 |
| MSSA (No. of strains | Reading 18 h | | 10/10 | 9/10 | 5/10 | 4/10 |
| detected/No. of strains) | Reading 24 h | | 10/10 | 9/10 | 6/10 | 4/10 |

TABLE 2e

Substitution of Cefoxitin with Cefpodoxime

| | Medium | T | E | | | |
|---|---|---|---|---|---|---|
| | Antibiotic | Cefoxitin | Cefpodoxime | | | |
| | Concentration (mg/l) | 4 | 0.5 | 1 | 1.5 | 2 |
| MRSA (No. of strains | Reading 18 h | 5/10 | 9/10 | 8/10 | 8/10 | 5/10 |
| detected/No. of strains) | Reading 24 h | 5/10 | 10/10 | 9/10 | 8/10 | 7/10 |
| MSSA (No. of strains | Reading 18 h | | 10/10 | 10/10 | 8/10 | 6/10 |
| detected/No. of strains) | Reading 24 h | | 10/10 | 10/10 | 8/10 | 6/10 |

TABLE 2f

Substitution of Cefoxitin with Cefdinir

| | Medium | T | L | | | | |
|---|---|---|---|---|---|---|---|
| | Antibiotic | Cefoxitin | Cefdinir | | | | |
| | Concentration (mg/l) | 4 | 0.25 | 0.5 | 1 | 2 | 4 | 8 |
| MRSA (No. of strains | Reading 18 h | 5/10 | 3/10 | 3/10 | 2/10 | | |
| detected/No. of strains) | Reading 24 h | 6/10 | 4/10 | 4/10 | 4/10 | 1/10 | |
| MSSA (No. of strains | Reading 18 h | | | | | | |
| detected/No. of strains) | Reading 24 h | | 5/10 | 1/10 | | | |

The antibiotics Cefoxatime, Ceftriaxone, Ertapenem, Cefpodoxime, Cefoperazone and Cefdinir did not make it possible to obtain, on their own, a sensitivity and a specificity enabling MRSAs to be distinguished from MSSAs.

3.3—Medium For Detecting MRSAs, Comprising A Combination of Antibiotics Selected From the Pairs Cefoxitin/Ceftriaxone, Cefoxitin/Cefotaxime, Cefoxitin/Ertapenem, Cefoxitin/Cefoperazone or Cefoxitin/Cefpodoxime The results obtained when combinations of antibiotics were used are given in table 3.

TABLE 3

Detection of MRSA colonies when a combination of antibiotics was used (detection expressed as number of strains detected per number of total strains)

| | Medium | T | F | | | | T | G | | |
|---|---|---|---|---|---|---|---|---|---|---|
| | Antibiotic 1 | Cefoxitin | Cefoxitin | | | | Cefoxitin | Cefoxitin | | |
| | Concentration Antibiotic 1 (mg/l) | 4 | 0.5 | 1 | 0.5 | 1 | 4 | 0.5 | 1 | 0.5 | 1 |
| | Antibiotic 2 | None | Cefotaxime | | | | None | Ceftriaxone | | |
| | Concentration Antibiotic 2 (mg/l) | 0 | 0.5 | 0.5 | 1 | 1 | 0 | 0.5 | 0.5 | 1 | 1 |
| MRSA | Reading 18 h | 6/10 | 9/10 | 8/10 | 6/10 | 5/10 | 6/10 | 9/10 | 8/10 | 9/10 | 8/10 |
| | Reading 24 h | 8/10 | 10/10 | 8/10 | 6/10 | 6/10 | 8/10 | 10/10 | 10/10 | 10/10 | 8/10 |
| MSSA | Reading 18 h | — | 4/10 | 1/10 | 1/10 | — | — | 6/10 | 4/10 | 4/10 | 3/10 |
| | Reading 24 h | — | 5/10 | 2/10 | 1/10 | — | — | 6/10 | 5/10 | 4/10 | 4/10 |

| | Medium | T | H | | | | | | | |
|---|---|---|---|---|---|---|---|---|---|---|
| | Antibiotic 1 | Cefoxitin | Cefoxitin | | | | | | | |
| | Concentration Antibiotic 1 (mg/l) | 4 | 0 | 0.5 | 0.5 | 0.5 | 0.5 | 0.75 | 0.75 | 0.75 | 0.75 |
| | Antibiotic 2 | None | Ertapenem | | | | | | | |
| | Concentration Antibiotic 2 (mg/l) | 0 | 1 | 0.25 | 0.5 | 0.75 | 1 | 0.25 | 0.5 | 0.75 | 1 |
| MRSA | Reading 18 h | 6/10 | 7/10 | 8/10 | 7/10 | 7/10 | 6/10 | 7/10 | 7/10 | 7/10 | 2/10 |
| | Reading 24 h | 6/10 | 8/10 | 8/10 | 8/10 | 8/10 | 7/10 | 8/10 | 8/10 | 8/10 | 4/10 |
| MSSA | Reading 18 h | — | 3/10 | 9/10 | 6/10 | 2/10 | — | 7/10 | 3/10 | 10/10 | — |
| | Reading 24 h | — | 5/10 | 9/10 | 8/10 | 5/10 | — | 10/10 | 6/10 | 10/10 | — |

| | Medium | T | I | | | | | | | |
|---|---|---|---|---|---|---|---|---|---|---|
| | Antibiotic 1 | Cefoxitin | Cefoxitin | | | | | | | |
| | Concentration Antibiotic 1 (mg/l) | 4 | 0 | 0.5 | 0.5 | 0.5 | 0.5 | 0.75 | 0.75 | 0.75 | 0.75 |
| | Antibiotic 2 | None | Cefpodoxime | | | | | | | |
| | Concentration Antibiotic 2 (mg/l) | 0 | 2 | 0.5 | 1 | 1.5 | 2 | 0.5 | 1 | 1.5 | 2 |
| MRSA | Reading 18 h | 5/10 | 5/10 | 8/10 | 5/10 | 5/10 | 1/10 | 6/10 | 5/10 | 4/10 | 1/10 |
| | Reading 24 h | 5/10 | 5/10 | 8/10 | 5/10 | 5/10 | 5/10 | 7/10 | 5/10 | 5/10 | 3/10 |
| MSSA | Reading 18 h | — | 4/10 | 6/10 | — | — | — | 2/10 | — | — | — |
| | Reading 24 h | — | 4/10 | 7/10 | 1/10 | — | — | 5/10 | — | — | — |

| | Medium | T | J | | | | | | | |
|---|---|---|---|---|---|---|---|---|---|---|
| | Antibiotic 1 | Cefoxitin | Cefoxitin | | | | | | | |
| | Concentration Antibiotic 1 (mg/l) | 4 | 0 | 0.5 | 0.5 | 0.5 | 0.5 | 0.75 | 0.75 | 0.75 | 0.75 |
| | Antibiotic 2 | None | Cefoperazone | | | | | | | |
| | Concentration Antibiotic 2 (mg/l) | 0 | 1.5 | 0.5 | 0.75 | 1 | 1.5 | 0.5 | 0.75 | 1 | 1.5 |
| MRSA | Reading 18 h | 5/10 | 5/10 | 6/10 | 5/10 | 5/10 | 2/10 | 5/10 | 5/10 | 5/10 | 1/10 |
| | Reading 24 h | 5/10 | 7/10 | 9/10 | 5/10 | 5/10 | 4/10 | 6/10 | 6/10 | 5/10 | 2/10 |
| MSSA | Reading 18 h | — | 6/10 | 4/10 | 3/10 | 2/10 | — | 4/10 | 3/10 | 1/10 | — |
| | Reading 24 h | — | 7/10 | 5/10 | 4/10 | 3/10 | 1/10 | 4/10 | 4/10 | 2/10 | 1/10 |

| | Medium | T | M | | | | | | | |
|---|---|---|---|---|---|---|---|---|---|---|
| | Antibiotic 1 | Cefoxitin | Cefoxitin | | | | | | | |
| | Concentration Antibiotic 1 (mg/l) | 4 | 0.25 | 0.5 | 0.75 | 0.25 | 0.5 | 0.75 | 0.25 | 0.5 | 0.75 |
| | Antibiotic 2 | None | Cefdinir | | | | | | | |
| | Concentration Antibiotic 2 (mg/l) | 0 | 0.1 | 0.1 | 0.1 | 0.25 | 0.25 | 0.25 | 0.5 | 0.5 | 0.5 |
| MRSA | Reading 18 h | 6/10 | 7/10 | 6/10 | 6/10 | 4/10 | 4/10 | 5/10 | 4/10 | 3/10 | 2/10 |
| | Reading 24 h | 7/10 | 8/10 | 7/10 | 7/30 | 4/10 | 5/10 | 5/10 | 4/10 | 4/10 | 4/10 |
| MSSA | Reading 18 h | — | 4/10 | 1/10 | 1/10 | — | — | — | 1/10 | 1/10 | — |
| | Reading 24 h | — | 5/10 | 1/10 | 1/10 | — | — | — | 1/10 | 1/10 | — |

The combinations of antibiotics above made it possible to obtain a greater specificity and a greater sensitivity than those obtained when a single antibiotic was used.

3.4—Medium For Detecting MRSAs, Comprising A Cefoxitin/Cefotaxime Antibiotic Combination And A Mixture of Inhibitors That Favour the Growth Of *Staphylococcus Aureus*

The results obtained when combinations of antibiotics were used are given in table 4.

TABLE 4

Detection of MRSA colonies when a Cefoxitin/Cefotaxime antibiotic combination per number of total strains and a mixture of inhibitors were used (detection expressed as number of strains detected per number of total strains)

| | Medium | T | | | K | | | |
|---|---|---|---|---|---|---|---|---|
| | Antibiotic 1 | Cefoxitin | | | Cefoxitin | | | |
| | Concentration Antibiotic 1 (mg/l) | 4 | 0.5 | 0.55 | 0.6 | 0.65 | 0.7 | 0.75 |
| | Antibiotic 2 | None | | | Cefotaxime | | | |
| | Concentration Antibiotic 2 (mg/l) | 0 | 0.75 | 0.75 | 0.75 | 0.75 | 0.75 | 0.75 |
| MRSA | Reading 18 h | 5/10 | 5/10 | 5/10 | 5/10 | 5/10 | 5/10 | 5/10 |
| | Reading 24 h | 9/10 | 8/10 | 9/10 | 8/10 | 8/10 | 8/10 | 9/10 |
| MSSA | Reading 18 h | — | — | — | — | — | — | — |
| | Reading 24 h | — | 3/10 | 2/10 | 1/10 | — | — | — |

The Cefoxitin/Cefotaxime antibiotic combination combined with a mixture of inhibitors that promote the growth of *Staphylococcus aureus* made it possible to obtain an excellent specificity and sensitivity.

EXAMPLE C

Medium According To the Invention, Comprising A Phosphatase Substrate

Experiments similar to those presented in example B were carried out, the alpha-glucosidase substrate being substituted with a phosphatase substrate, 6-chloro-3-indoxyl phosphate (phosphate pink), the antibiotic combination being Cefoxitin and Cefotaxime.

The results obtained are given in table 5.

TABLE 5

Detection of MRSA colonies when a phosphatase substrate and a cefoxitin/cefotaxime antibiotic combination was used

| | Medium | T | | | M | | | |
|---|---|---|---|---|---|---|---|---|
| | Antibiotic 1 | Cefoxitin | | | Cefoxitin | | | |
| | Concentration Antibiotic 1 (mg/l) | 4 | 0.75 | 0.75 | 0.75 | 0.75 | 1 | 1 |
| | Antibiotic 2 | None | Cefotaxime | | | | | |
| | Concentration Antibiotic 2 (mg/l) | 0 | 0 | 0.5 | 0.75 | 1 | 0.5 | 0.75 |
| MRSA | Reading 18 h | 10/10 | 10/10 | 9/10 | 10/10 | 10/10 | 10/10 | 10/10 |
| | Reading 24 h | 10/10 | 10/10 | 9/10 | 10/10 | 10/10 | 10/10 | 10/10 |
| MSSA | Reading 18 h | | 10/10 | | | | | |
| | Reading 24 h | | 10/10 | 2/10 | | | | |

The Cefoxitin/Cefotaxime antibiotic combination combined with the substrate 6-chloro-3-indoxyl phosphate (phosphate pink) made it possible to obtain an excellent specificity and sensitivity.

The invention claimed is:

1. A reaction medium for detecting and/or identifying Methicillin-resistant *Staphylococcus aureus* (MRSA) bacteria, comprising a) a predetermined combination of two antibiotics, a first antibiotic which belongs to the cephalosporin family and a second antibiotic, wherein said first and second antibiotics are each at a sub-inhibitory concentration for Methicillin-sensitive *Staphylococcus aureus* (MSSA); and b) a substrate for detecting an enzymatic or metabolic activity of said MRSA.

2. The reaction medium according to claim 1, wherein said first antibiotic belongs to the cephamycin subfamily.

3. The reaction medium according to claim 1, wherein said second antibiotic belongs to the carbapenem family.

4. The reaction medium according to claim 1, wherein said second antibiotic belongs to the cephalosporin family.

5. The reaction medium according to claim 1, wherein said substrate is for detecting a glycosidase, esterase or peptidase enzymatic activity.

6. The reaction medium according to claim 5, wherein said substrate is for detecting an alpha-glucosidase enzymatic activity.

7. The reaction medium according to claim 1, wherein said substrate is for detecting carbohydrate metabolic activity.

8. The reaction medium according to claim 1, further comprising a second substrate for detecting an enzymatic or metabolic activity.

9. The reaction medium according to claim 8, wherein said second substrate is for detecting an alpha-glucosidase enzymatic activity.

10. The reaction medium according to claim 4, wherein said first and/or second antibiotic(s) belonging to the cephalosporin family is selected from:
a first-generation cephalosporin;
a second-generation cephalosporin;
a third-generation cephalosporin; and
a fourth-generation cephalosporin.

11. The reaction medium according to claim 3, wherein said second antibiotic belonging to the carbapenem family is selected from Meropenem, Ertapenem and Imipenem.

12. The reaction medium according to claim 1, wherein the combination of two antibiotics is a) Cefoxitin and Cefotaxime; or b) Cefoxitin and Ertapenem.

13. A method for detecting and/or identifying Methicillin-resistant *Staphylococcus aureus* (MRSA) bacteria, in a biological sample, comprising:
   a) inoculating the biological sample on a reaction medium according to claim 1;
   b) incubating the biological sample; and
   c) identifying colonies on the reaction medium as being MRSA colonies when MRSA bacteria is present in the biological sample.

* * * * *